United States Patent [19]

Nishizono

[11] Patent Number: 5,498,310
[45] Date of Patent: Mar. 12, 1996

[54] APPLICATION SYSTEM FOR APPLICATION STRIP ATTACHED CONDOMS

[75] Inventor: Taiji Nishizono, Kuki, Japan

[73] Assignee: K. K. Chibaminato Shoji, Chiba, Japan

[21] Appl. No.: 276,175

[22] Filed: Jul. 15, 1994

[51] Int. Cl.⁶ .............................. B65B 61/14; A61F 6/04
[52] U.S. Cl. ........................... 156/513; 29/795; 128/844; 156/60; 604/349
[58] Field of Search .............................. 156/60, 160, 229, 156/513, 514; 29/791, 792, 795, 783, 787; 128/844; 604/349

[56]  References Cited

U.S. PATENT DOCUMENTS

| | | |
|---|---|---|
| 3,018,484 | 1/1962 | Koehn . |
| 4,607,474 | 8/1986 | Jarvis ......................... 53/117 |
| 4,731,064 | 3/1988 | Heyden . |
| 4,872,463 | 10/1989 | Nishizono ...................... 128/844 |
| 4,945,923 | 8/1990 | Evans et al. . |
| 4,972,850 | 11/1990 | Broad ......................... 128/844 |
| 4,987,905 | 1/1991 | Broad ......................... 128/844 |
| 5,165,422 | 11/1992 | Broad, Jr. ................... 128/844 |

FOREIGN PATENT DOCUMENTS

| | | |
|---|---|---|
| 358095 | 3/1990 | European Pat. Off. . |
| 2649315 | 1/1991 | France . |
| 2650178 | 2/1991 | France . |
| 2661819 | 11/1991 | France . |
| 1026044 | 3/1958 | Germany . |
| 2410697 | 12/1974 | Germany . |
| 3737908 | 5/1989 | Germany . |
| 59-211448 | 11/1984 | Japan . |
| 2153686 | 8/1985 | United Kingdom . |
| 2225721 | 6/1990 | United Kingdom . |
| WO9008522 | 8/1990 | WIPO . |
| WO9313734 | 7/1993 | WIPO . |

Primary Examiner—Michael W. Ball
Assistant Examiner—Daniel J. Stemmes
Attorney, Agent, or Firm—Juettner Pyle Lloyd & Piontek

[57] ABSTRACT

It is the object of the present invention to provide a condom application strip attaching system capable of automatically attaching a condom application strip having a slit adapted to accept a semen-storing receptacle within a condom. A mandrel to be covered with a condom is vertically attached on the outer margin of a rotating turntable which is indexed to stop at predetermined positions for predetermined times. A manipulating arm support is arranged inside the turntable corresponding to the mandrel. A first condom unrolling device, a second condom unrolling device, a condom application strip manufacturing device, a pressing device, a pair of flat spatulas, a first condom rolling device, a second condom rolling device, and a condom removing device are arranged in sequence outside and along the turntable to effect the entwining of a condom application strip within a condom.

20 Claims, 6 Drawing Sheets

APPLICATION SYSTEM FOR APPLICATION STRIP ATTACHED CONDOMS

FIELD OF THE INVENTION

The present invention relates to an apparatus and method for mechanically manufacturing a condom especially adapted for convenient application to a body member of a user. More particularly, the present invention provides an apparatus for automatically applying a condom application strip on opposite sides along the length of a condom and rolling same to be entwined with the condom prior to packaging, in order to facilitate later unrolling of the condom for use.

BACKGROUND OF THE INVENTION

Various condoms containing unfurling tapes or strips have recently been proposed and disclosed. An example of such condoms is set forth in Nishizono U.S. Pat. No. 4,872,463, and the disclosure of same is incorporated herein in its entirety by reference. These strips, situated along the length of the cylindrical portion of the condom, are typically applied to the condom by hand, a labor intensive, time consuming and inefficient process.

SUMMARY OF THE INVENTION

In accordance with the present invention, an apparatus and method is provided for automatically unrolling a pre-formed condom on a mandrel, applying an application strip along opposite longitudinal sides of a cylindrical portion thereof, and then rerolling and removing the condom with application strip rolled therein.

The present invention comprises a rotatable turntable having a plurality of vertically extending mandrels or solid forms for supporting a pre-formed condom having a semen receptacle in an unrolled condition. The turntable is indexed to stop sequentially at a number of stations for a predetermined time interval for performing the various tasks required. Each of the mandrels have a protrusion for engaging the semen receptacle of the condom and to retain the condom in position. As arm support device is attached to the turntable at a position radially inward from and corresponding to each of the condom mandrels for manipulating the condom and the application strip.

The preferred device includes two stations for unrolling the condom over the mandrel using mechanized rollers to thereby define a first end condom portion having the semen-storing receptacle and a cylindrical condom portion. A subsequent station includes a condom application strip fabrication device for automatically forming the application strip and simultaneously providing a central longitudinal slit centrally located therein by cutting a sheet-like tape. The application strip is then placed over the semen-storing receptacle of the condom and the condom protrusion. At the next station, a pressing pipe presses the strip carried on the condom to protrude the semen-storing receptacle of the condom through the slit of the application strip. A subsequent station smooths the distal ends of the strip along the length of the cylindrical portion of the condom, followed by stations having roller devices for rerolling the condom with the strip entwined therein. A removal device removes the rolled condom and the entwined application strip combination from the condom mandrel by grasping the exposed central portion of the strip or the protruding semen-storing receptacle.

In accordance with the forgoing, an object of the present invention is to provide an apparatus for the manufacture of condoms having unfurling tapes or strips for subsequent ease of application by users.

A further object of the present invention is to provide an efficient apparatus for automatically disposing within a such packaged condom unfurling tapes or strips.

DETAILED DESCRIPTION OF THE PREFERRED EMBODIMENT

The following is a description of the best mode presently contemplated by the inventor for carrying out his invention. Other modes of carrying out the invention, without departing from the scope of the invention, will become apparent to those skilled in the art as the description proceeds.

Figure 8:
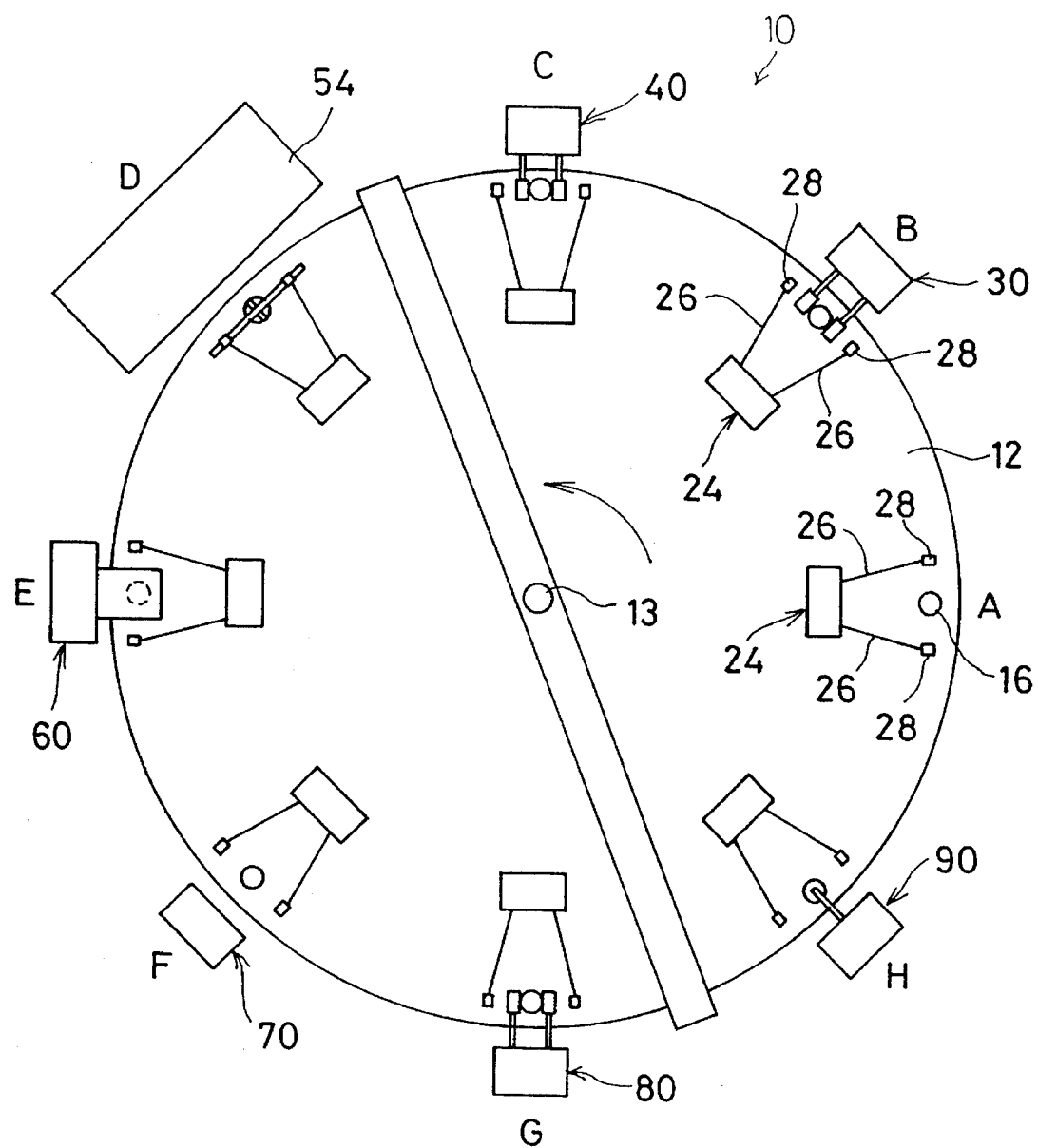
FIG. 8 is schematic top view of the condom application strip attaching system of the present invention.

FIG. 8 schematically shows the overall apparatus of the present invention, which includes a circular turntable 12 supported by a shaft 13 and rotated by a drive means (not shown) in the direction of the arrow. The turntable 12 is sequentially rotated at fixed angular intervals about its axis. It is indexed to stop sequentially at a first station A, a second station B, a third station C, a fourth station D, a fifth station E, a sixth station F, a seventh station G and an eighth station H over a single rotation.

Figure 7:
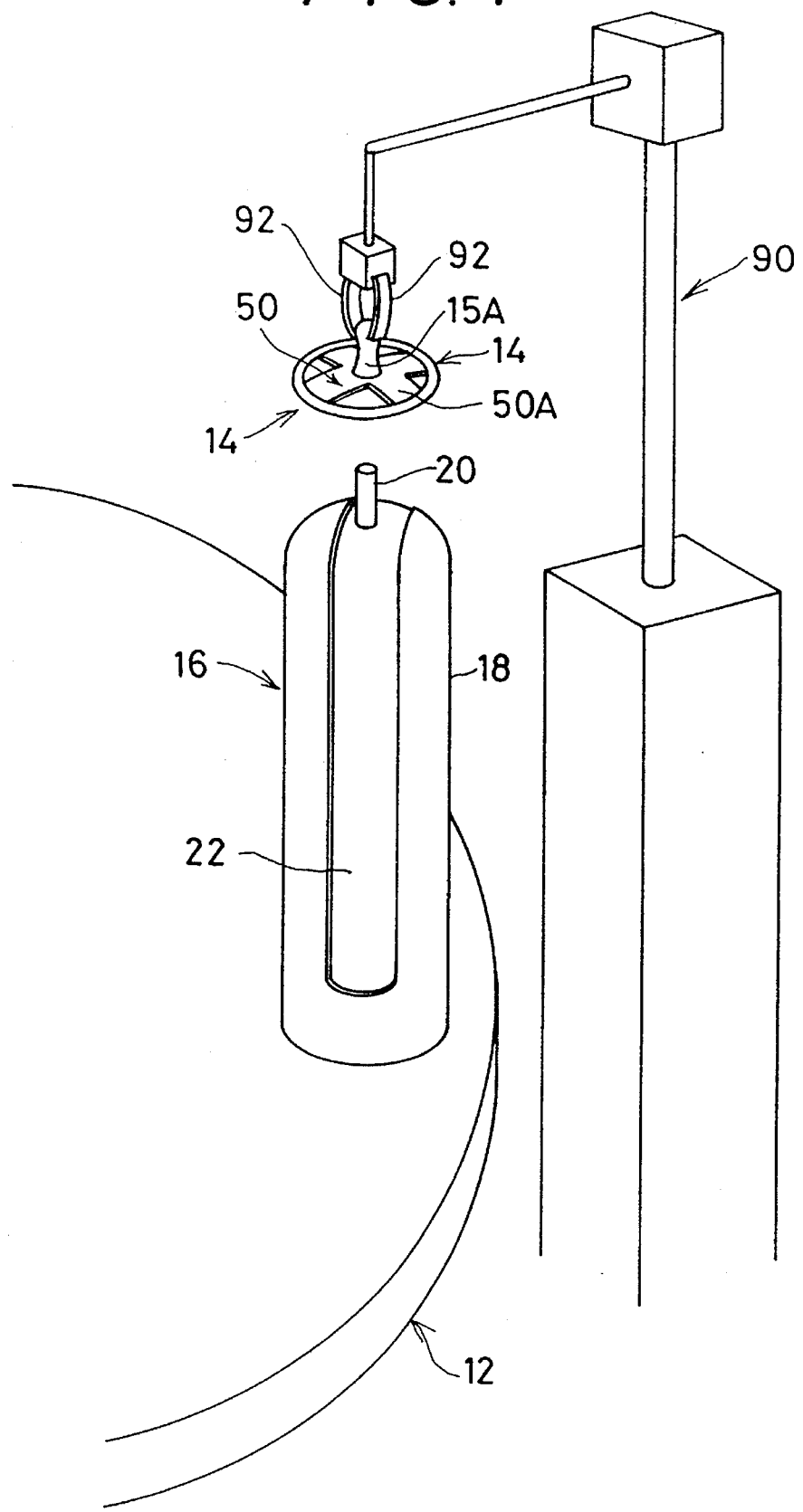
FIG. 7 is a perspective view of the eighth station, including a condom removing means, of the preferred embodiment of the present invention.

Preferably eight mandrels or solid forms 16 are disposed regularly about the outer periphery of the turntable 12, and each are adapted to receive a pre-formed condom 15, a component of the product manufactured in accordance with the present invention, to wit, a condom-strip assembly 14 (see FIG. 7). As better shown in FIG. 1, the mandrel 16 is provided with a protrusion 20, having an outer diameter adapted for insertion into a semen-storing receptacle 15A of the condom 15 as the condom 15 is placed on the mandrel 16. A groove portion 22 is formed longitudinally on a cylindrical portion 18 of the mandrel 16, as will be discussed further below.

As shown in FIG. 8, a manipulating arm support 24 serves as an operation device and is arranged radially inward from each mandrel 16. A pair of arms 26 are located on the support 24 such that the arms 26 may move vertically and horizontally relative the mandrel. An attracting and pressing portion 28 is forming at the tip of each of the arms 26. A hole (not shown) is formed on the attracting and pressing portion 28 so as to attract an object by a vacuum device included in the support 24.

Figure 2:
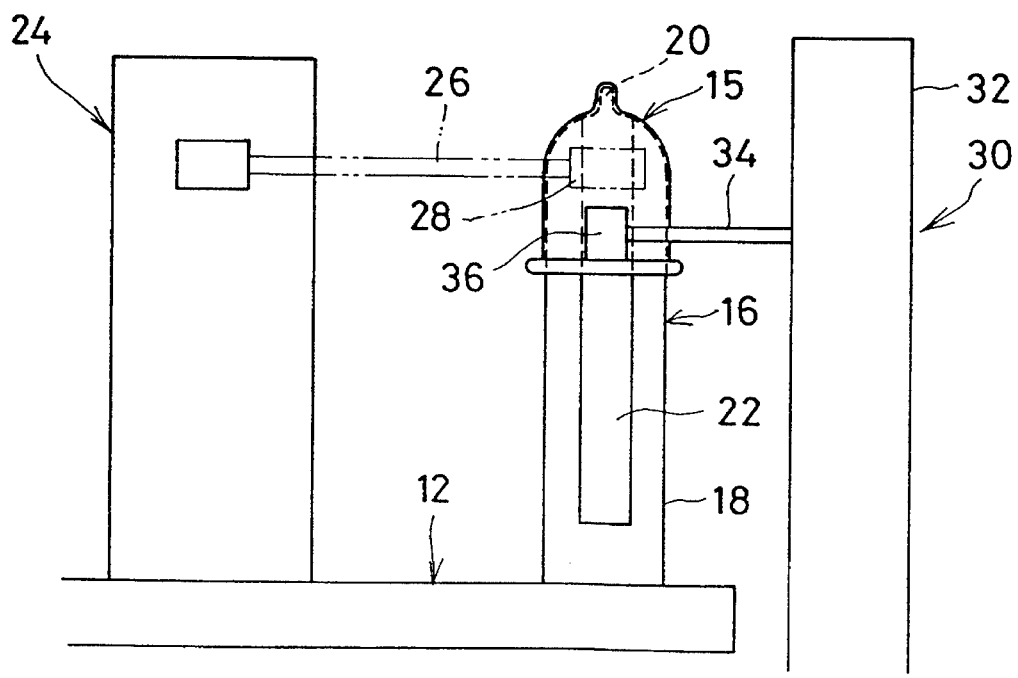
FIG. 2 is a side view of the second station, including a primary unrolling means, of the preferred embodiment of the present invention.

As shown in FIG. 2, a primary condom unrolling device 30 is arranged at the second station B outside the turntable 12. The primary condom unrolling device 30 unrolls the cylindrical portion 15B of the condom 15 up to the middle of the portion 15B. The primary condom spreading device 30 comprises a first tower 32, a first pair of roller arms 34 moving vertically relative the first tower 32, and a first pair of rollers 36 rotatably attached to the tip of the first pair of roller arms 34.

Figure 3:
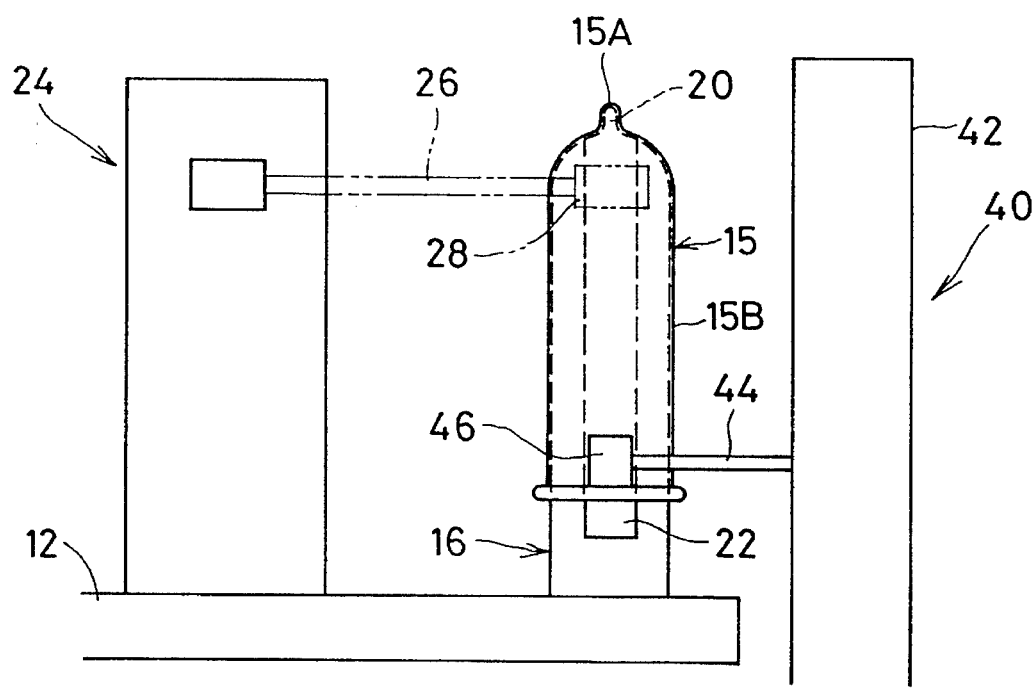
FIG. 3 is a side view of the third station, including a secondary unrolling means, of the preferred embodiment of the present invention.

As shown in FIG. 3, a second condom unrolling device 40 is provided at the third station C outside the turntable 12. The second condom unrolling device 40 further unrolls the cylindrical portion 15B of the condom 15 half-unrolled by the first condom unrolling device 30 up to the end of the portion of the condom. The second condom unrolling device 40 comprises a second tower 42, a second pair of roller arms 44 moving vertically relative to the second tower 42, and a second pair of rollers rotatably attached to the tip of the second pair of roller arms 44.

Figure 4:
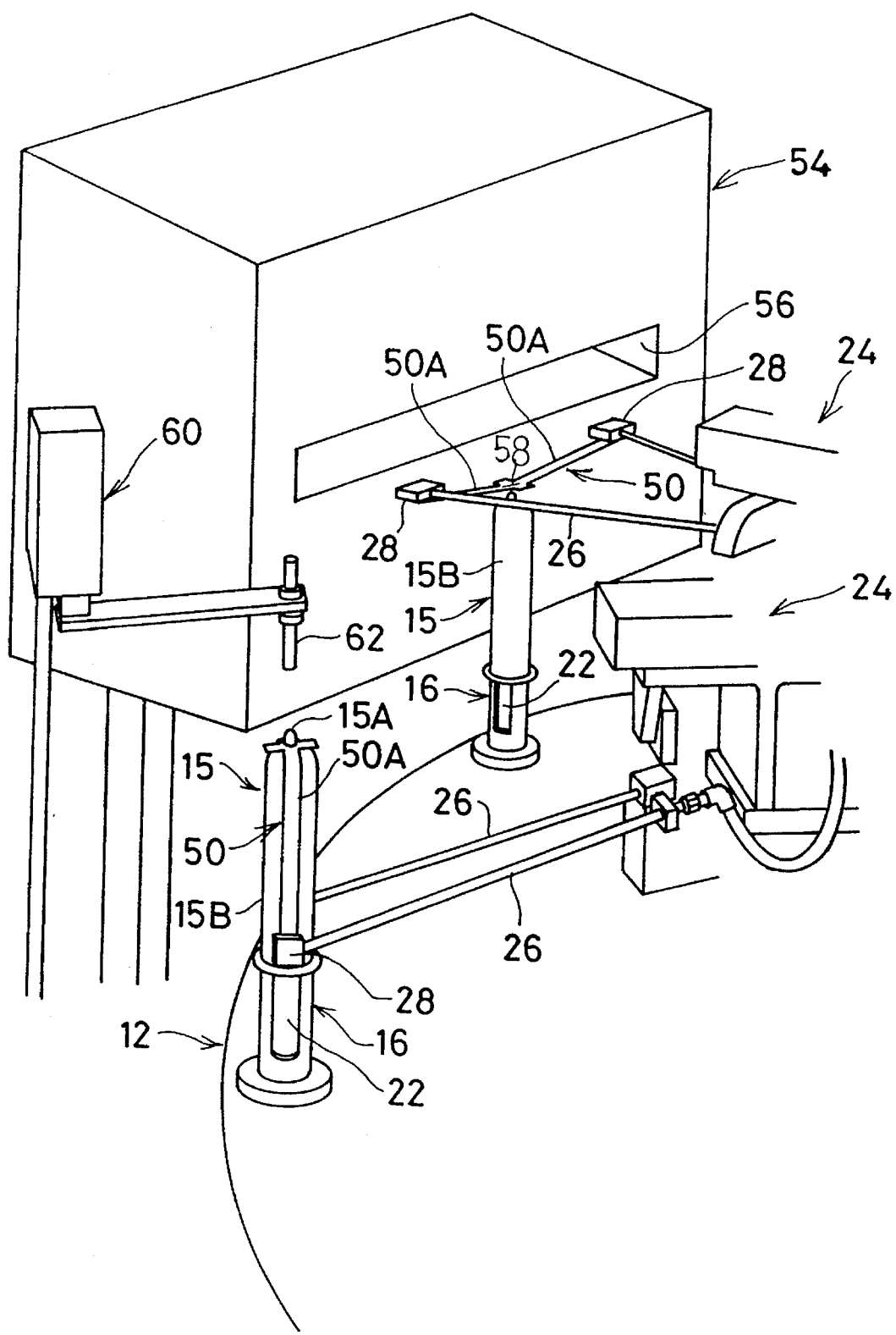
FIG. 4 is a perspective view of the fourth and fifth stations, including the strip application means, of the preferred embodiment of the present invention.

As shown in FIG. 4, an application strip fabrication device 54 is provided to automatically fabricate a condom application strip 50 at the fourth station D outside the turntable 12. A tape sheet (not shown) serving as the material of the strip 50 is housed in the device 54. A cutter therein cuts the tape sheet into an approximate cross to fabricate the strip 50 and simultaneously forms a slit 58 at a central portion of the strip 50. At the fourth station D, the strip 50 is also placed on the semen-storing receptacle of the condom 15 by the attracting and pressing portion 28 of the arms 24.

A pressing device 60 is arranged at the fifth station E outside the turntable 12, following the fourth station D. Station F is provided to press downward on the central portion of the strip 50, mounted on the condom 15, through a pressing pipe 62 attached to the pressing device 60 and capable of moving vertically. The inside diameter of the pressing pipe 62 is slightly larger than the outside diameter of the protrusion 20 and semen-storing receptacle. Therefore, as the pressing pipe 62 presses downward on the central portion of the strip 50, the protrusion 20 and semen-storing receptacle are forced to protrude outside through the slit 58 of the strip 50.

Figure 5:
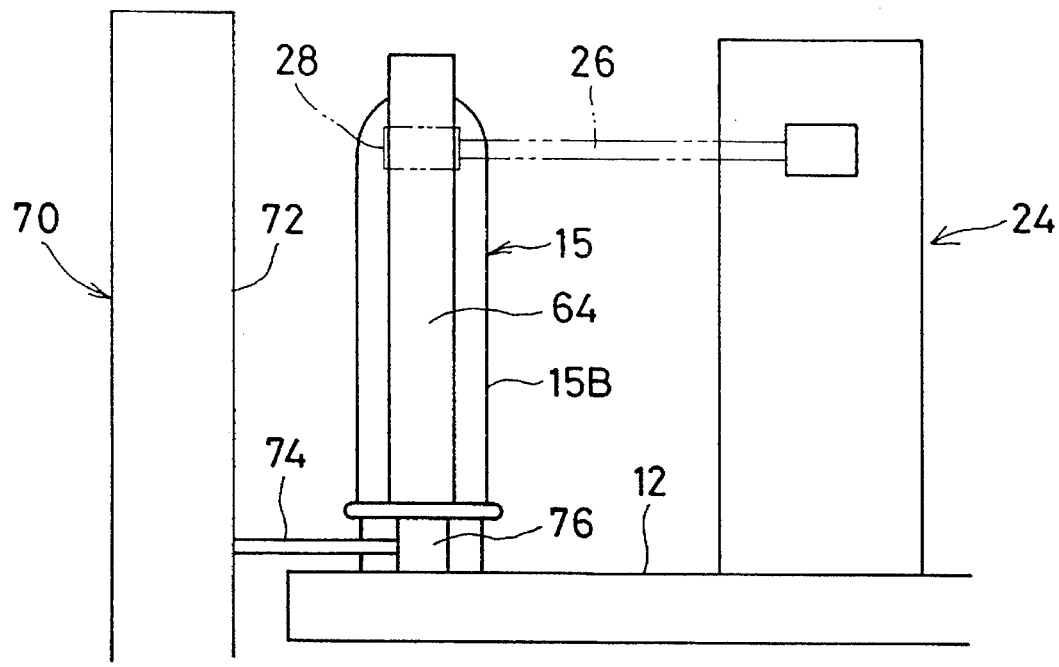
FIG. 5 is a side view of the sixth station, including a primary rolling means, of the preferred embodiment of the present invention.

As shown in FIG. 5, a pair of flat spatulas 64 press either distal ends 50A of the strip 50 from both sides at the sixth station F. The spatulas 64 are arranged so that they can move vertically to urge the distal ends 50A of the strip 50 against the cylindrical portion 15B of the condom 15.

A first condom rolling device 70 is arranged at the sixth station F outside the turntable 12. The first condom rolling device 70 comprises a first tower 72, a first pair of roller arms 74 capable of moving vertically relative the first tower 72, and a first pair of rollers 76 rotatably mounted on the tip of the first pair of roller arms 74.

Figure 6:
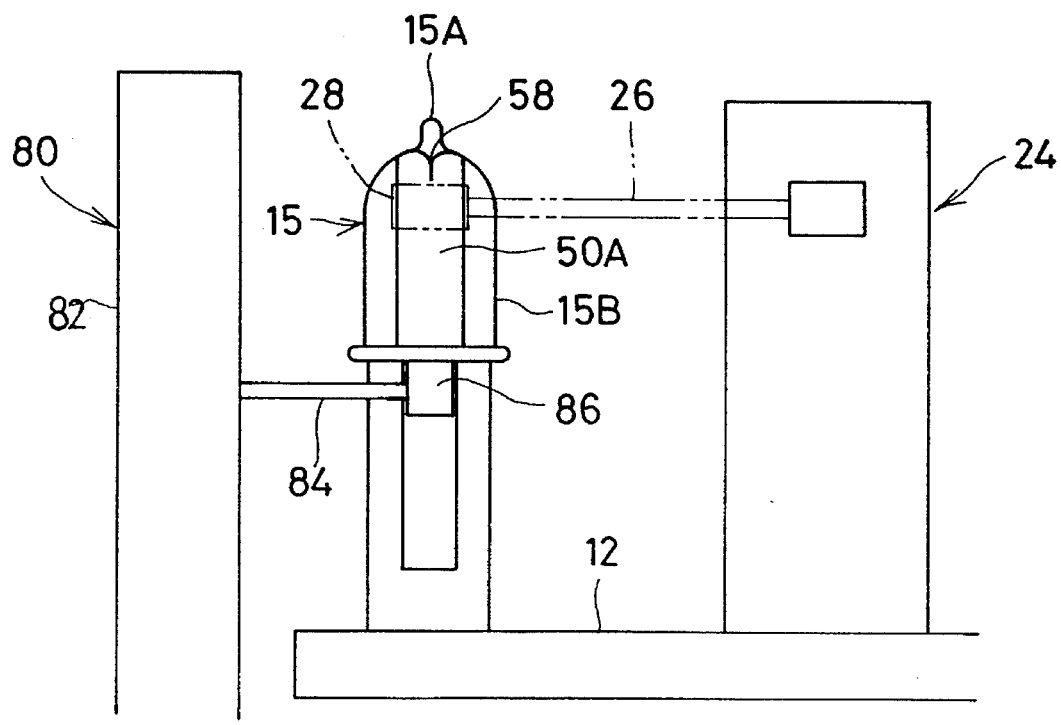
FIG. 6 is a side view of the seventh station, including a secondary rolling means, of the preferred embodiment of the present invention.

As shown in FIG. 6, a second condom rolling device 80 is arranged at the seventh station G outside the turntable 12. The second condom rolling device 80 rolls the cylindrical portion of the condom 15 half-rolled by the first condom rolling device 70 up to the first end near the semen-storing receptacle. The second condom rolling device 80 comprises a second tower 82, a second pair of roller arms 84 capable of moving vertically relative the second tower 82, and a second pair of rollers 86 rotatably set at the tips of the second pair of roller arms 84.

As shown in FIG. 7, a condom grasping device 90 is arranged at the eighth position H outside the turntable 12. The condom grasping device 90 has a pair of holding claws 92 capable of grasping a condom 14 by the central portion of the condom application strip to remove the condom 14 from the mandrel 16.

Figure 1:
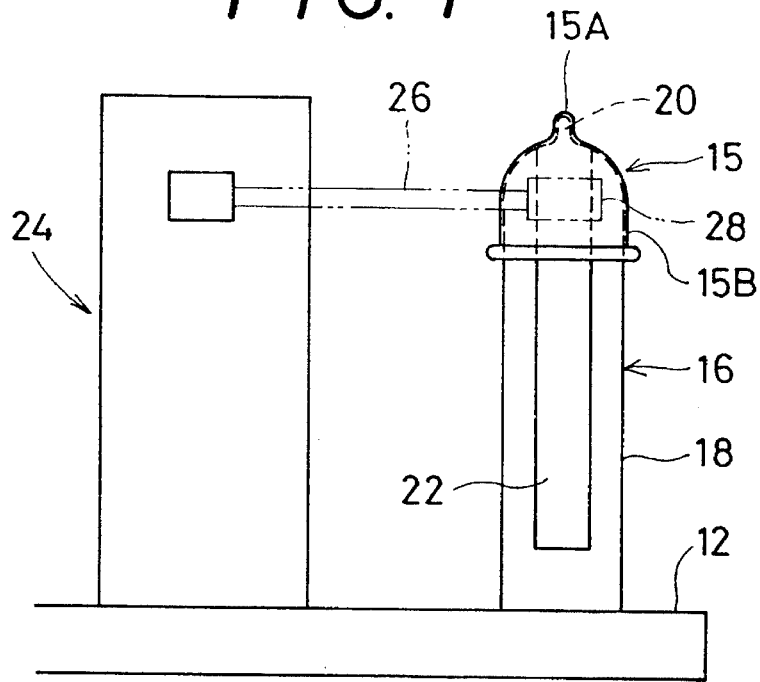
FIG. 1 is a side view of the condom support means of the preferred embodiment of the present invention at the first station.

The operation of the present invention begins as shown in FIG. 1, when the turntable 12 stops at the first station A. An operator places a rolled pre-formed condom 15 whose cylindrical portion 15B is to be unrolled on the mandrel 16.

Next, the turntable 12 is rotated and stops as the mandrel 16 and condom 15 is moved to second station B. Then, as shown in FIG. 2, the pair of roller arms 34 of the first condom unrolling device 30 at the second position B move downward and the first pair of rollers 36 contact the rolled cylindrical portion 15B of the condom 15 to unroll the cylindrical portion 15B to approximately the middle of its longitudinal length.

The turntable 12 is then further rotated to move the mandrel 16 to the third station C. As shown in FIG. 3, the second pair of roller arms 44 of the second condom unrolling device 40 arranged at the third position C move downward and the second pair of rollers 46 engage the cylindrical portion 15B of the condom 15 to further unroll the remaining rolled cylindrical portion 15B up to the end of the condom.

The turntable 12 is then rotated until the mandrel reaches the fourth station D. As shown in FIG. 4, the arms 26 extend to enter an opening 56 of the application strip fabrication device 54, where the attracting and pressing portion 28 vacuum-attracts the distal ends 50A of the strip 50, previously cut into a cross shape and simultaneously provided with a central longitudinal slit 58 in the application strip fabrication device 54. The arms 26 then carry the strip 50 to place it on the semen-storing receptacle on the mandrel 16.

The turntable 12 is further rotated to the fifth station E. There, the pressing pipe 62 of the pressing device 60 moves downward against the mandrel 16 to press the central portion of the strip 50. Thus, the protrusion 20 of the mandrel 16 is forced into the interior of the pressing pipe 62 and passes through the slit 58 of the strip 50. As a result, the semen-storing receptacle 15A of the condom 15 is caused to protrude through the slit 58. The arms 26 then vacuum-attract the distal ends 50A of the strip 50 to lower and attach the distal ends 50A to and along the cylindrical portion 15B of the condom 15.

The turntable 12 is then rotated to the sixth station F. There, as shown in FIG. 5, the spatulas 64 press the distal ends 50A of the strip 50 from both sides to attach the distal ends 50A to the cylindrical portion 15B of the condom 15.

The first pair of roller arms 74 of the first condom rolling device 70 then moves upward and the first pair of rollers 76 roll the cylindrical portion 15B of the condom 15 up to approximately its mid-point. At this point, the distal ends 50A of the strip 50 are entwined into and rolled together with the cylindrical portion 15B.

Next, the turntable 12 is rotated to the seventh station G. As shown in FIG. 6, the second pair of roller arms 84 of the second condom rolling device 80 arranged at the seventh position G move upward and the second pair of rollers 86 completely roll the cylindrical portion 15B of the condom 15 and the distal ends 50A of the strip 50 up. Thereby, the condom 14 with a condom application strip is manufactured.

The turntable 12 is then rotated to the eighth station H. There, as shown in FIG. 7, the holding claws 92 of the condom grasping device 90 grasp the semen-storing receptacle 15A of the condom 15 and remove the condom 14 with a condom application strip from the condom pattern 16 to house the condom 14 in a storage vessel (not-illustrated) or the like.

The turntable 12 is then rotated to the first station A, where the operator again covers the mandrel 16 with the pre-formed rolled condom 15. The above operations are then repeated.

The remaining seven mandrels 16 also perform the same function to attach the strip 50 to the condom 15. Therefore, it is possible to greatly improve the efficiency of manufacturing the condom 14 with a condom application strip. As shown in the preferred embodiment, eight mandrels 16 are attach on the turntable 12. However, the number of condom patterns is not restricted to eight.

As described above, the present invention makes it possible to attach a condom application strip to a condom automatically. Therefore, the present invention has an excellent advantage capable of further improving the efficiency of manufacturing a condom with a condom application strip.

The objects and advantages of the invention have thus been shown to be attained in an economical, practical and facile manner.

While a preferred embodiment of the invention has been herein illustrated and described, it is to be appreciated that various chambers, rearrangements and modifications may be made therein, without departing from the scope of the invention as defined by the appended claims.

What is claimed is:

1. An apparatus for manufacturing condom assemblies including a rolled condom and application strips entwined within the condom, the apparatus comprising:

a rotatable turntable indexed to stop at a plurality of predetermined stations for a predetermined time interval;

a vertically extending mandrel attached to the turntable and adapted to receive on a distal end thereof a rolled condom;

manipulating means attached to the turntable at a position radially inward from and corresponding to the mandrel;

unrolling means for unrolling the rolled condom over the mandrel and thereby defining a first end portion having a semen-storing receptacle and a cylindrical condom portion;

application strip fabricating means for forming the application strip by cutting a tape, the application strip having two distal ends and a central portion having a slit, and cooperating with the manipulating means for placing the application strip on the first end portion of the condom;

pressing means for pressing the strip onto the first end of the condom and for forcing the semen-storing receptacle of the condom to protrude through the slit of the application strip;

application strip pressing means for attaching the distal ends of the strip to opposite sides of the cylindrical portion of the condom;

rolling means for rolling the cylindrical portion of the condom and for entwining the distal ends of the application strip therein; and removing means for removing the rolled condom and application strip assembly from the mandrel.

2. The apparatus of claim 1, wherein the manipulating means attached to the turntable includes a pair of arms adapted to move vertically and horizontally relative the mandrel, each arm further having attracting and pressing means formed at a distal end thereof.

3. The apparatus of claim 2, wherein the attracting means on each of the distal ends of the arms includes a hole so as to attract the condom and the application strips by a vacuum means provided in the manipulating means.

4. The apparatus of claim 1, wherein the unrolling means and rolling means includes a pair of arms adapted to move vertically and horizontally relative the mandrel, each arm further having a roller means formed at a distal end thereof for urging the cylindrical portion of the condom into an unrolled and rolled condition, respectively.

5. The apparatus of claim 1, wherein the application strip lateral pressing means for attaching the distal ends of the strip to opposite sides of the cylindrical portion of the condom includes a pair of spatulas disposed to press against the distal ends of the strip and press the same against the cylindrical portion of the condom.

6. The apparatus of claim 1, wherein the removing means for removing the rolled condom and application strip assembly from the condom mandrel includes a pair of holding claws adapted to grasp the assembly to remove the assembly condom from the mandrel.

7. An apparatus for manufacturing packaged condom assemblies comprising a condom and application strips entwined therein, the apparatus comprising:

a rotatable turntable indexed to stop at a plurality of predetermined positions for a predetermined time interval;

a vertically extending condom mandrel attached to the turntable and adapted to receive thereon a rolled condom;

an arm support attached on the turntable at a position radially inward from and corresponding to the condom mandrel for manipulating the application strip;

an unrolling device for unrolling a cylindrical portion of the of the rolled condom, and thereby defining a first end portion having a semen-storing receptacle and a cylindrical condom portion;

a condom application strip fabricating device for forming the application strip and providing a slit centrally located therein by cutting a tape and for cooperation with the manipulating means for placing the application strip on the semen-storing receptacle of the condom;

a pressing device for pressing the strip carried onto the condom pattern from the top to protrude the semen-storing receptacle of the condom from the slit of the application strip;

a condom application strip pressing device for attaching a portion of the application strip to the cylindrical portion of the condom;

a rolling device for rolling the cylindrical portion of the condom and the attached portion of the application strip; and a removing device for removing the rolled condom and the entwined portion of the application strip from the condom mandrel.

8. The apparatus of claim 7, wherein the arm support attached to the turntable includes a pair of arms adapted to move vertically and horizontally relative the mandrel, each arm further having attracting and pressing means formed at a distal end thereof.

9. The apparatus of claim 8, wherein the attracting means on each of the distal ends of the arms includes a hole so as to attract the condom and the application strips by vacuum means provided in the manipulating means.

10. The apparatus of claim 7, wherein the unrolling and rolling devices include a pair of arms adapted to move vertically and horizontally relative the mandrel, each arm further having a roller means formed at a distal end thereof for urging the cylindrical portion of the condom into an unrolled and rolled condition, respectively.

11. The apparatus of claim 7, wherein the condom strip pressing device includes a pair of spatulas disposed to press against the distal ends of the strip and press the same against the cylindrical portion of the condom.

12. The apparatus of claim 7, wherein the removing device includes a pair of holding claws adapted to grasp the condom assembly to remove the condom assembly from the condom mandrel.

13. An apparatus for manufacturing condom assemblies including a rolled condom and application strips entwined within the condom, the apparatus comprising:

a rotatable turntable indexed to stop at a plurality of predetermined stations for a predetermined time interval;

a vertically extending mandrel attached to the turntable and adapted to receive on a distal end thereof a rolled condom. the mandrel having an upwardly projecting central protrusion;

manipulating means attached to the turntable at a position radially inward from and corresponding to the mandrel;

unrolling means for unrolling the rolled condom over the mandrel and thereby defining a first end portion having a semen-storing receptacle and a cylindrical condom portion;

application strip fabricating means for forming the application strip by cutting a tape, the application strip having two distal ends and a central portion having a slit, and cooperating with the manipulating means for placing the application strip on the first end portion of the condom;

pressing means for pressing the strip onto the first end of the condom and for forcing the semen-storing receptacle of the condom to protrude through the slit of the application strip, the pressing means cooperating with the upwardly projecting central protrusion provided on the mandrel, the upwardly projecting protrusion having an outside diameter adapted to accept the semen-storing receptacle of the condom, and the pressing means having a circular depression for receiving the protrusion, the circular depression having an inside diameter slightly larger than the outside diameter of the upwardly projecting central protrusion of the mandrel, such that when the pressing means is brought into contact with the condom, the protrusion and semen-storing receptacle protrude through the slit of the strip;

application strip pressing means for attaching the distal ends of the strip to opposite sides of the cylindrical portion of the condom;

rolling means for rolling the cylindrical portion of the condom and for entwining the distal ends of the application strip therein; and removing means for removing the rolled condom and application strip assembly from the mandrel.

14. The apparatus of claim 13, wherein the manipulating means attached to the turntable includes a pair of arms adapted to move vertically and horizontally relative the mandrel, each arm further having attracting and pressing means formed at a distal end thereof.

15. The apparatus of claim 14, wherein the attracting means on each of the distal ends of the arms includes a hole so as to attract the condom and the application strips by a vacuum means provided in the manipulating means.

16. The apparatus of claim 13, wherein the unrolling means and rolling means includes a pair of arms adapted to move vertically and horizontally relative the mandrel, each arm further having a roller means formed at a distal end thereof for urging the cylindrical portion of the condom into an unrolled and rolled condition, respectively.

17. The apparatus of claim 13, wherein the application strip lateral pressing means for attaching the distal ends of the strip to opposite sides of the cylindrical portion of the condom includes a pair of spatulas disposed to press against the distal ends of the strip and press the same against the cylindrical portion of the condom.

18. The apparatus of claim 13, wherein the removing means for removing the rolled condom and application strip assembly from the condom mandrel includes a pair of holding claws adapted to grasp the assembly to remove the assembly condom from the mandrel.

19. An apparatus for manufacturing condom assemblies comprising a condom and application strips entwined therein, the apparatus comprising:

a rotatable turntable indexed to stop at a plurality of predetermined positions for a predetermined time interval;

a vertically extending condom mandrel attached to the turntable and adapted to receive thereon a rolled condom, the mandrel having an upwardly projecting central protrusion;

a rotatable turntable indexed to stop at a plurality of predetermined positions for a predetermined time interval;

an arm support attached on the turntable at a position radially inward from and corresponding to the condom mandrel for manipulating the application strip;

an unrolling device for unrolling a cylindrical portion of the of the rolled condom and thereby defining a first end portion having a semen-storing receptacle and a cylindrical condom portion;

a condom application strip fabricating device for forming the application strip and providing a slit centrally located therein by cutting a tape and for cooperation with the manipulating means for placing the application strip on the semen-storing receptacle of the condom;

a pressing pipe device for pressing the strip carried onto the condom mandrel from the top to protrude the semen-storing receptacle of the condom from the slit of the application strip, the upwardly projecting central protrusion of the condom mandrel having an outside diameter adapted to accept the semen-storing receptacle of the condom, and the pressing pipe device including a pipe portion adapted to receive the protrusion having an inside diameter slightly larger than the outside diameter of the upwardly projecting central protrusion of the condom mandrel, such that when the pressing pipe device is brought into contact with the condom, the protrusion and semen-storing receptacle protrude through the slit of the strip into the pipe portion:

a condom application strip pressing device for attaching a portion of the application strip to the cylindrical portion of the condom:

a rolling device for rolling the cylindrical portion of the condom and the attached portion of the application strip; and a removing device for removing the rolled condom and the entwined portion of the application strip from the condom mandrel.

20. A method for manufacturing condom assemblies including a rolled condom and application strips entwined within the condom, the method comprising the steps of:

rotating a turntable having mounted thereon a vertically extending condom mandrel, the turntable being indexed to stop at a plurality of predetermined positions for a predetermined time interval and the mandrel adapted to receive on a distal end thereof a rolled condom;

unrolling the rolled condom to thereby define a first end portion having a semen-storing receptacle and a cylindrical condom portion;

forming the application strip by cutting a tape, the application strip having two distal ends and a central portion having a slit, and placing the application strip on the first end portion of the condom;

pressing the strip onto the first end of the condom and forcing the semen-storing receptacle of the condom to protrude through the slit of the application strip;

pressing the distal ends of the strip against opposite sides of the cylindrical portion of the condom;

rolling the cylindrical portion of the condom and entwining the distal ends of the application strip therein; and removing the rolled condom and application strip assembly from the condom mandrel.

* * * * *